United States Patent [19]
Hwu et al.

[11] Patent Number: 5,733,890
[45] Date of Patent: Mar. 31, 1998

[54] ADENYLATE ANALOGS AS POTENT ANTI-HERPES VIRUS AGENTS

[75] Inventors: Jih Ru Hwu; Gholam H. Hakimelahi, both of Taipei; Shwu-Chen Tsay, Hsinchu, all of Taiwan; Ali A. Moosavi-Movahedi, Tehran; Majid M. Sadeghi, Isfahan, both of Islamic Rep. of Iran

[73] Assignee: National Science Council, Taipei, Taiwan

[21] Appl. No.: 727,292

[22] Filed: Oct. 9, 1996

[51] Int. Cl.⁶ .......................... A61K 31/70; C07H 19/19; C07H 19/20
[52] U.S. Cl. .................... 514/47; 514/68; 514/70; 514/81; 536/25.6; 536/26.5; 536/27.4; 544/264
[58] Field of Search .............................. 536/25.6, 26.5, 536/27.4; 544/264; 514/47, 68, 70, 81

[56] References Cited

PUBLICATIONS

Hakimelahi et al., "Design Synthesis, and Structure–Activity Relationship of Novel Dinucleotide Analogues as Agents Against Herpes and Human Immunodeficiency Viruses," *J. Medicinal Chem.*, 38(23), 4648–4659 (Nov. 10, 1995).
Rosenberg et al., "Phosphonylmethoxyalkyl and Phosphonylalkyl Derivatives of Adenine," *Coll. Czech. Chem. Comm.*, 53(11B), 2753–2777 (Nov. 1988).

*Primary Examiner*—John Kight
*Assistant Examiner*—L. Eric Crane
*Attorney, Agent, or Firm*—Hitt Chwang & Gaines P.C.

[57] ABSTRACT

Novel adenylate analogs having the following formula are synthesized in the present invention, which are found active against herpes simplex viruses:

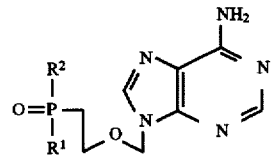

wherein $R^1$ is hydroxyl, $C_1$–$C_4$ alkoxy, an amino ester radical of —$NHR^3COOR^4$, wherein $R^3$ is a bivalent $C_1$–$C_4$ saturated hydrocarbon and $R^4$ is $C_1$–$C_4$ alkyl; and $R^2$ is hydroxyl, —$O^+NH_4$ or

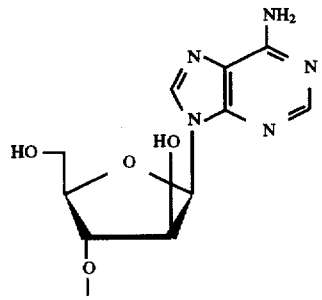

12 Claims, No Drawings

ADENYLATE ANALOGS AS POTENT ANTI-HERPES VIRUS AGENTS

FIELD OF THE INVENTION

The present invention is related generally to synthesis of novel adenylate analogs and their pharmaceutical use, and more particularly to synthesis of novel adenylate analogs which are active against herpes simplex viruses (HSV).

BACKGROUND OF THE INVENTION

Acyclic adenosine VI [Schaeffer, H. J., et al. Novel Substrate of Adenosine Deaminase. J. Med. Chem. 1971, 14, 367–369] and 9-(β-D-arabinofuranosyl)adenine 37 (arabinoside, Ara-A) [Shannon, W. M. In Adenine Arabinoside, an Antiviral Agent, Pavan-Langston, D.; Buchanan. R. A.; Alford, C. A., Eds. Raven Press, New York, 1975, pp 1–44] can inhibit viral replication. However, Ara-A is also known being able to be converted in vivo to hypoxanthine (Ara-Hx) via deamination by adenosine deaminase, which adversely affects the activity of Ara-A in inhibition of viral replication. Ara-A is also potent in treating a patient having acute type B hepatitis. In addition to the deamination, the potency of Ara-A is also reduced due to its poor lipophilicity.

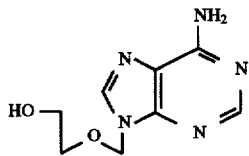
(VI)

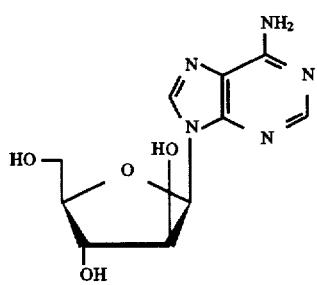
(37)

SUMMARY OF THE INVENTION

The present invention discloses a novel adenylate analog having the following formula:

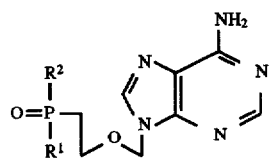
(I)

wherein $R^1$ is hydroxyl, $C_1$–$C_4$ alkoxy, an amino ester radical of —$NHR^3COOR^4$, wherein $R^3$ is a bivalent $C_1$–$C_4$ saturated hydrocarbon and $R^4$ is $C_1$–$C_4$ alkyl; and $R^2$ is hydroxyl, —$O^+NH_4$ or

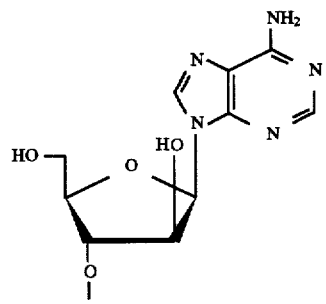

or pharmaceutically acceptable salts thereof.

Preferably, $R^1$ of the adenylate analog of formula I is methyl L-alaninate [(L)-$NHCHCH_3CO_2CH_3$].

Preferably, $R^2$ of the adenylate analog of formula I is

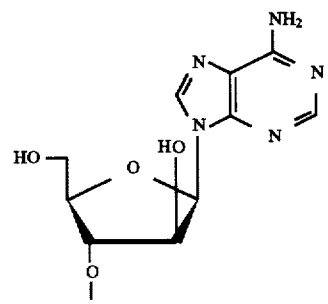

The present invention also provides a pharmaceutical composition for the treatment of a human infected by a herpes simplex virus (HSV) comprising a therapeutically effective amount of the adenylate analog of the formula I or a pharmaceutically acceptable salt thereof, as an active ingredient, in admixture with a pharmaceutically acceptable carrier or diluent for the active ingredient.

The present invention further provides a method for the treatment of a human infected by a herpes simplex virus (HSV) comprising administering a therapeutically effective amount of the adenylate analog of the formula I to a human infected by a herpes simplex virus (HSV).

The adenylate analog of the formula I synthesized in accordance with the present invention is found potent in inhibiting cytopathogenicity of herpes simplex type 1 virus (HSV-1), herpes simplex type 2 virus (HSV-2) and varicella-zoster virus (VZV) in Hela cell culture, and having a low cellular toxicity.

In the preferred embodiments of the present invention, the following adenylate analogs 12, 13, 40 and 42 were synthesized. Compounds 12 and 13 of the adenylate analogs are nucleotide analogs, and the compounds 40 and 42 are dinucleotide analogs.

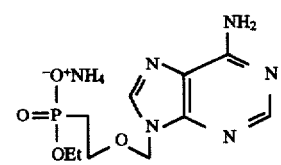
(12)

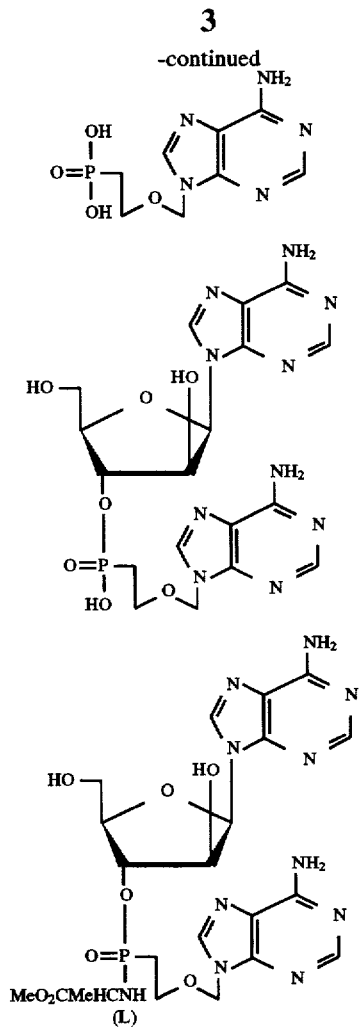

pyridine, and THF (see Scheme 7). We then condensed the resultant 2',5'-disilyl ether 38 (97%) with phosphonic acid 13 by using trichloromethanesulfonyl chloride in collidine and THF to afford nucleotide phosphonate 39 in 55% yield. Desilylation of 39 with (n-Bu)$_4$NF at 25° C. gave the target molecule 40 in 78% yield.

We condensed nucleotide phosphonate 39 with methyl L-alaninate by using (triisopropyl)benzenesulfonyl chloride to give a diastereoisomeric mixture of phosphonoamidates 41 (1:1) in 97% yield. Compounds 41 showed two close signals at δ38.71 and 38.80 ppm in its $^{31}$P NMR spectrum, resulting from the phosphonoamidate chiral center. Desilylation of 41 with (n-Bu)$_4$NF afforded the target phosphonoamidate 42 in 90% yield.

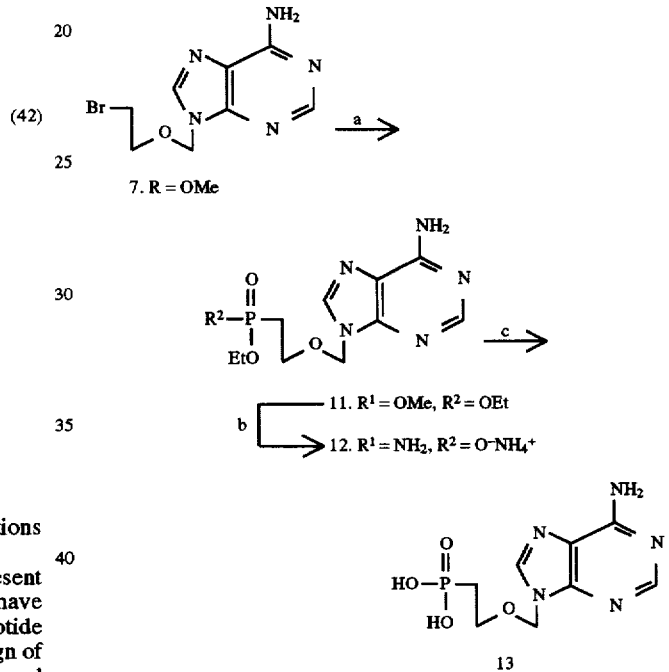

Reagents: (a) (EtO)$_3$P, Δ; (b) NH$_3$, MeOH; (c) Me$_3$SiBr, DMF wherein Me is methyl and Et is ethyl (these abbreviations also apply in the following text).

Among the adenylate analogs synthesized in the present invention, the dinucleotide analogs are believed to have better antiherpes virus activity compared to the nucleotide analogs. The former are synthesized according to a design of combination therapy, wherein acyclic adenosine VI and Ara-A 37 are connected with a phosphonate structure. Moreover, the dinucleotide analogs show a superior lipophilicity and water solubility, when R$^1$ in the formula I is the amino ester radical, which enhance the efficiency of the transport of the adenylate analogs through the cell membranes, and thus increases its antiherpes virus activity and its ability to inhibit the deamination caused by adenosine deaminase.

Synthesis of Acyclic Nucleoside Phosphonate 13 (Scheme 1)

We carried out the Arbuzov reaction [Holy, A. Synthesis of 5'-Deoxyuridine 5'-Phosphonic Acid. Tetrahedron Lett. 1967, 881–884] by treatment of acyclonucleoside 7 with triethyl phosphite to produce the desired diethyl phosphonate 11. Reaction of 11 with NH$_3$ in MeOH gave monoammonium salt 12 in 40% yield. We then treated 12 with Me$_3$SiBr in DMF to provide a 45% yield of the desired phosphonate 13, which may exist in its zwitterionic form.

Syntheses of Phosphonate 40 as well as Phosphonoamidate 42 (Scheme 7)

The dinucleotide phosphonate 40 was readily obtained in three steps from arabinoadenosine 37, which was first silylated with (t-Bu)Me$_2$SiCl in the presence of AgNO$_3$,

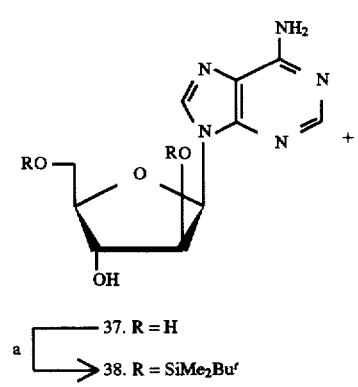

-continued
Scheme 7

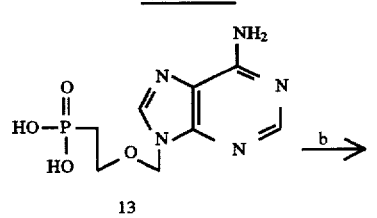

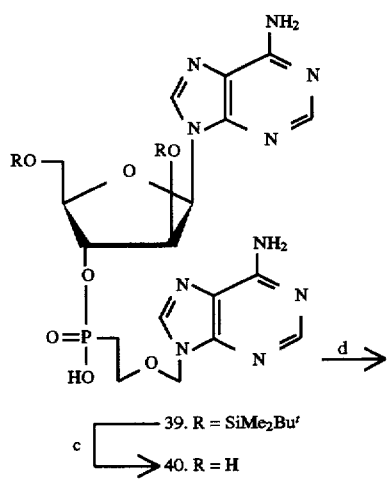

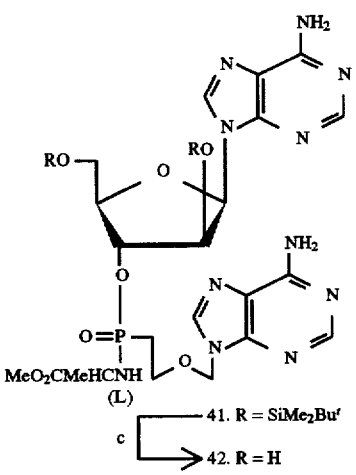

Reagents: (a) t-BuMe$_2$SiCl, AgNO$_3$, pyridine, THF; (b) CCl$_3$SO$_2$Cl, collidine, THF; (c) (n-Bu)$_4$NF, THF; (d) 2,4,6-triisopropylbenzenesulfonyl chloride, methyl L-alaninate, pyridine.

The invention will be further illustrated by the following examples which are only meant to illustrate the invention, but not to limit it. The reaction routes for synthesizing the title compounds of the Preparation Examples 1–3 and 4–7 are shown in the Schemes 1 and 7, respectively.

PREPARATION EXAMPLE 1

Diethyl [2-[(6-Methoxypurin-9-yl)methoxy]ethyl] phosphonate (11)

A mixture of 7 (2.87 g, 10.0 mmol) and triethyl phosphite (8.30 g, 50.0 mmol) was heated at 150° C. for 24 h. Ether (300 mL) was added to the solution at room temperature and the resultant precipitate was filtered. Crystallization from a mixture of MeOH and Et$_2$O (1:4) gave 11 (1.01 g) in 30% yield: mp 140°–141° C.; TLC Rf 0.17 (AcOEt/MeOH=4:1); UV $\lambda_{max}$(EtOH): 249 nm ($\epsilon$12 250); $^1$H NMR (CDCl$_3$): δ1.10–1.54 (m, 8 H, 2×CH$_3$+CH$_2$P), 3.39–4.30 (m, 6 H, 2×CH$_2$OP+CH$_2$O), 4.15 (s, 3 H, OCH$_3$), 5.61 (s, 2 H, OCH$_2$N), 8.12, 8.41 (2 s, 2 H, HC(2)+HC(8)). Anal. (C$_{13}$H$_{21}$N$_4$O$_5$P) C, H, N.

PREPARATION EXAMPLE 2

Ammonium Ethyl [2-[(Adenin-9-yl)methoxy]ethyl] phosphonate (12)

To a solution of 11 (3.44 g, 10.0 mmol) in MeOH (40 mL) was added a saturated methanolic NH$_3$ solution (100 mL). The solution was heated in a sealed flask at 100° C. for 30 h. The solvent was evaporated and the residue was crystallized from EtOH to give 12 (1.20 g) in 40% yield: mp 190°–193° C.; TLC Rf 0.37 (AcOEt/MeOH=1:1); UV $\lambda_{max}$ (EtOH): 260 nm ($\epsilon$14 000); $^1$H NMR (DMSO-d$_6$/D$_2$O): δ1.20–1.56 (m, 5 H, CH$_3$+CH$_2$P), 3.40–4.10 (m, 2 H, CH$_2$OP), 4.30 (m, 2 H, CH$_2$O), 5.60 (s, 2 H, OCH$_2$N), 7.80, 8.12 (2 s, 2 H, HC(2) +HC(8)). Anal. (C$_{10}$H$_{19}$N$_6$O$_4$P) C, H, N.

PREPARATION EXAMPLE 3

2-[(Adenin-9-yl)methoxy]ethylphosphonic Acid (13)

To a solution of 12 (0.32 g, 1.0 mmol) in DMF (7.0 mL) was added Me$_3$SiBr (1.07 g, 7.01 mmol). After the solution was stirred at 40° C. for 6 h, a mixture of MeOH and H$_2$O(5:1, 20 mL) was added and the solvents were evaporated. The crude residue was purified by use of column chromatography (resin XAD-4, H$_2$O) to afford 13 (0.12 g, 45%): mp 296° C. (dec.); TLC Rf 0.32 (MeOH); UV $\lambda_{max}$ (EtOH): 259 nm ($\epsilon$13 700); $^1$H NMR(DMSO-d$_6$/D$_2$O): δ1.49 (m, 2 H, CH$_2$P), 3.80 (m, 2 H, CH$_2$O), 5.55 (s, 2 H, OCH$_2$N), 7.90, 8.19 (2 s, 2 H, HC(2)+HC(8)). Anal. (C$_8$H$_{12}$N$_5$O$_4$P) C, H, N.

PREPARATION EXAMPLE 4

9-[2',5'-Bis-O-(tert-butyldimethylsilyl)-β-D-arabinofuranosyl]adenine-3'-[[2-(adenin-9-ylmethoxy)ethyl]phosphonate] (39)

Collidine (0.61 g, 5.0 mmol) was added to a solution of THF (2.0 mL) containing 13 (0.27 g, 0.99 mmol) at −10° C. To this solution was added CCl$_3$SO$_2$Cl (0.22 g, 1.0 mmol) in THF (0.50 mL) dropwise. After 38 (0.50 g, 1.0 mmol) in THF (2.0 mL) was added into the mixture, it was stirred at 25° C. for 10 h. The solvents were removed and the residue was dissolved in AcOEt (20 mL) and washed with H$_2$O (20 mL). The organic layer was concentrated and the residue was purified by use of preparative TLC with a mixture of CHCl$_3$ and MeOH (6:1) as the eluant. The band at Rf ca. 0.50 was eluted with AcOEt to afford 39 (0.41 g) in 55% yield: mp 129°–131° C.; TLC Rf 0.50 (CHCl$_3$/MeOH=6:1); UV $\lambda_{max}$ (EtOH): 259 nm ($\epsilon$17 500); $^1$H NMR(DMSO-d$_6$/D$_2$O): δ0.15 (br s, 12 H, 2×(CH$_3$)$_2$Si), 0.90, 1.15 (2 s, 18 H, 2×(CH$_3$)$_3$C), 1.68 (m, 2 H, CH$_2$P), 3.81–4.26 (m, 4 H, CH$_2$O+H$_2$C(5')), 4.31–4.76 (m, 3 H, HC(2')+HC(3')+HC(4') ), 5.61 (s, 2 H, OCH$_2$N), 6.57 (d, J=4.8 Hz, 1 H, HC(1')), 8.01, 8.12, 8.52, 8.71 (4 s, 4 H, 2×HC(2)+2×HC(8)); $^{31}$P NMR (DMSO-d$_6$): δ29.20. Anal. (C$_{30}$H$_{51}$N$_{10}$O$_7$PSi$_2$) C, H, N.

PREPARATION EXAMPLE 5

9-(β-D-Arabinofuranosyl)adenine-3'-[[2-(Adenin-9-ylmethoxy)ethyl]phosphonate] (40)

To a solution of 39 (0.37 g, 0.49 mmol) in THF (3.0 mL) was added (n-Bu)$_4$NF (1.0M solution in THF, 0.31 g, 1.2 mmol). Acetic acid (0.50 mL) was added to the mixture after it was stirred at 25° C. for 30 min. The solvents were removed and the residue was purified by use of Whatman 3-mm paper with a mixture of i-PrOH, NH$_4$OH, and H$_2$O (9:1:2) as the eluant. The band at Rf ca. 0.42 was eluted with H$_2$O and collected by lyophilization to give 40 (0.20 g) in 78% yield: mp>250° C. (dec.); UV $\lambda_{max}$ (EtOH): 258 nm (ε18 000); $^1$H NMR (DMSO-d$_6$/D$_2$O): δ1.59 (m, 2 H, CH$_2$P), 3.78–4.12 (m, 4 H, CH$_2$O+H$_2$C(5')), 4.28–4.75 (m, 3 H, HC(2')+HC(3')+HC(4')), 5.59 (s, 2 H, OCH$_2$N), 6.50 (d, J=4.3 Hz, 1 H, HC(1')), 7.99, 8.18, 8.60, 8.80(4s, 4H, 2×HC(2)+2×HC(8)); $^{31}$P NMR (DMSO-d$_6$): δ29.25. Anal. (C$_{18}$H$_{23}$N$_{10}$O$_7$P) C, H, N.

PREPARATION EXAMPLE 6

9-[2',5'-Bis-O-(tert-butyldimethylsilyl)-β-D-arabinofuranosyl]adenine-3'-[(Methoxyalaninyl)[2-(adenin-9-ylmethoxy)ethyl]phosphonates] (Diastereoisomeric Mixture; 41)

To a solution of 39 (0.75 g, 1.0 mmol) in pyridine (6.0 mL) was added 2,4,6-(triisopropyl)benzenesulfonyl chloride (0.54 g, 1.8 mmol). After the mixture was stirred at 25° C. for 13 h, methyl L-alaninate (0.26 g 2.5 mmol) in pyridine (2.0 mL) was added and the mixture was stirred at 25° C. for 4 h. The solvent was removed and the residue was dissolved in AcOEt (30 mL). The organic layer was washed with H$_2$O (2×30 mL), dried, and concentrated. The residue was purified by use of preparative TLC with a mixture of CHCl$_3$ and MeOH (6:1) as the eluant. The band at Rf ca. 0.69 was eluted with a mixture of AcOEt and CHCl$_3$ (2:1) to afford 41 (0.81 g) in 97% yield: TLC Rf 0.69 (CHCl$_3$/MeOH=6:1); UV $\lambda_{max}$ (EtOH): 260 nm (ε17 800); $^1$H NMR (CDCl$_3$/DMSO-d$_6$/D$_2$O): δ0.16, 0.18 (2 s, 12 H, 2×(CH$_3$)$_2$Si), 0.83, 1.06 (2 s, 18 H, 2×(CH$_3$)$_3$C), 1.42 (d, J=5.8 Hz, 3 H, CH$_3$), 1.69 (m, 2 H, CH$_2$P), 3.68–4.25 (m, 8 H, CH$_3$O+CH$_2$O+CH+H$_2$C(5')), 4.33–4.78 (m, 3 H, HC(2')+HC(3') +HC(4')), 5.62 (s, 2 H, OCH$_2$N), 6.56 (d, J=4.9 Hz, 1 H, HC(1')), 8.06, 8.13, 8.54, 8.73 (4 s, 4 H, 2×HC(2)+2×HC(8)); $^{31}$P NMR (DMSO-d$_6$) δ38.71, 38.80. Anal. (C$_{34}$H$_{58}$N$_{11}$O$_8$PSi$_2$) C, H, N.

PREPARATION EXAMPLE 7

9-(β-D-Arabinofuranosyl)adenine-3'-[(Methoxyalaninyl)[2-(adenin-9-ylmethoxy)ethyl]phosphonates] (Diastereoisomeric Mixture; 42)

Compound 42 was obtained from 41 (1.20 g, 1.43 mmol) by following the procedure for preparation of 40 from 39. The crude material was purified by use of TLC plates and eluted with a mixture of CHCl$_3$ and MeOH (6:1). The desired product 42 (0.78 g) was isolated in 90% yield: TLC Rf 0.16 (CHCl$_3$/MeOH=6:1); paper chromatography, Rf 0.62 (i-PrOH/NH$_4$OH/H$_2$O=9:1:2); UV $\lambda_{max}$ (EtOH): 259 nm (ε18 760); $^1$H NMR (DMSO-d$_6$/D$_2$O): δ1.40 (d, J=5.9 Hz, 3 H, CH$_3$), 1.66 (m, 2 H, CH$_2$P), 3.70–4.10 (m, 8 H, CH$_3$O+CH$_2$O+CH+H$_2$C(5')), 4.32–4.76 (m, 3 H, HC(2')+HC(3')+HC(4')), 5.59 (s, 2 H, OCH$_2$N), 6.51 (d,J=4.3 Hz, 1 H, HC(1')), 8.05, 8.14, 8.56, 8.76 (4 s, 4 H, 2×HC(2)+2×HC(8)); $^{31}$P NMR(DMSO-d$_6$): 38.70, 38.82. Anal. (C$_{22}$H$_{30}$N$_{11}$O$_8$P) C, H, N.

EXAMPLE 1

Kinetic Studies of Competitive Inhibition of Adenosine Deaminase by Nucleoside and Nucleotide Analogs By following an established procedure [Ogilvie, K. K.; Nguyen-Ba, N.; Gillen, M. F.; Radatus, B. K.; Cheriyan, U. O.; Hanna, H. R.; Smith, K. O.; Galloway, K. S. Synthesis of A Purine Acyclonucleoside Series Having Pronounced Antiviral Activity. The Glyceropurines. Can. J. Chem. 1984, 62, 241–252.], we determined the rates of deamination of VI, 13, 37, 40, and 42 in the presence of calf mucosal adenosine deaminase (EC 3.5.4.4) in buffer solutions. Inhibition studies on these compounds were carried out on the basis of the Kaplan method (Moosavi-Movahedi, A. A.; Rahmani, Y.; Hakimelahi G. H., Thermodynamic and Kinetic Studies of Competitive Inhibition of Adenosine Deaminase by Ring Open Analogues of Adnine Nucleotides. Int. J. Biol. Micromol. 1993, 15,125–129). The results are shown in Table 1.

TABLE 1

| Substrate Activities and Inhibitory Properties against Adenosine Deaminase | | | |
|---|---|---|---|
| substrate | K$_m$ (μM) | rel V$_{max}$ | K$_I$ (μM) |
| 13 | 247.5 | 1.49 × 10$^{-6}$ | 18.2 |
| 40 | 166.2 | 7.64 × 10$^{-2}$ | |
| 42 | * | * | |
| VI | 138.0 | 1.52 × 10$^{-2}$ | 142.5 |
| 37 | 45.3 | 1 | |

*No reaction at 1500 μM.

We found that acyclonucleoside VI and acyclic nucleoside phosphonate 13 were adenosine deaminase substrates. The V$_{max}$ of 13 was, however, ~10$^{-4}$ times less than that of VI. Compounds VI and 13 showed competitive inhibition of adenosine deaminase when Ara-A 37 was used as a substrate. Nevertheless, phosphonate 13 acted more efficiently than acyclonucleoside VI as an inhibitor of adenosine deaminase. Nucleotide analog 40 was also a substrate of adenosine deaminase, but its V$_{max}$ was 92% less than that of Ara-A 37. The slow rate of deamination of compound 40 towards adenosine deaminase may reflect the inhibitory action of the acyclic nucleotide moiety therein at the active site of the enzyme. Subsequently, by assaying against calf mucosal adenosine deaminase in vitro, we found that phosphonoamidate 42 completely resisted deamination.

EXAMPLE 2

Determination of Solubility and Partition Coefficients (Lipophilicity) of Adenylate Analogs Determination of Solubility Each compound (70 mg) listed in Table 2 was agitated in a 25-mL volumetric flask with phosphate buffer (0.10M, 5.0 mL) for 20 h. This solution was filtered from undissolved solid through a sintered glass funnel (4.0–5.5 mesh ASTM) and the concentration of the solution was determined by UV absorbance (Table 2).

Determination of Partition Coefficients (Lipophilicity)

A solution of each compound (10 mL) in Table 2 in phosphate buffer (0.10M) possessing an UV absorbance of 2.2–3.3 at 258–265 nm was shaken with 1-pentanol (10 mL) in a separatory funnel for 1.5 h. The layers were separated, and their concentrations were determined by an UV spectrophotometer. The partition coefficient was calculated as P=[S]$_{1-pentanol}$/[S]H$_2$O (Table 2).

TABLE 2

Solubility in H₂O and Lipophilicity of Nucleoside and Nucleotide Analogs

| compound | solubility in H₂O (mg/mL) | log P[a] |
|---|---|---|
| 13 | 13.64 | 0.07 |
| 40 | 2.46 | −0.68 |
| 42 | 8.25 | 0.87 |
| VI | 1.95 | 0.98 |
| 37 | 0.40 | −0.47 |

[a]Partition coefficients were calculated as follows:
P = [Substrate]$_{1\text{-pentanol}}$/[Substrate]$_{H_2O}$.

We found from Table 2 that compounds 13, 40 and 42 synthesized in accordance with the present invention had partition coefficients ranging from 0.1 to 10, and had a higher water solubility.

EXAMPLE 3

Anti-Herpes and Anticellular Activities of Nucleoside and Nucleotide Analogs in Tissue Culture We tested the synthesized compounds for their inhibition of cytopathogenicity of herpes simplex type 1 virus (HSV-1), herpes simplex type 2 virus (HSV-2), and varicella-zoster virus (VZV) in Hela cell culture. These compounds include VI, 12, 13, 40, 42, a mixture of VI and 13 (1:1), ara-A 37, and a mixture of 13 and 37 (1:1). Toxicity of these compounds was evaluated by their ability to cause morphological changes in cells at different concentrations. The minimum inhibitory concentrations (IC$_{50}$), measured by use of the linear regression method, are summarized in Table 3.

TABLE 3

Anti-Herpes and Anticellular Activities of Nucleoside and Nucleotide Analogs in Tissue Culture

| | IC$_{50}$ (μg/ml)[a] | | | |
|---|---|---|---|---|
| compounds | HSV-1 (KOS) | HSV-2 (G) | VZV (YS) | Hela cell[b] |
| 12 | 11.26 | 13.80 | 25.00 | 175.60 |
| 13 | 3.98 | 5.86 | 16.00 | 215.00 |
| 40 | 8.97 | 16.29 | c | 346.07 |
| 42 | 0.38 | 0.88 | 4.82 | 215.48 |
| VI | 4.43 | 8.26 | 6.50 | 265.70 |
| 37 | 10.80 | c | c | 98.85 |
| 13 + VI (1:1) | 0.15 | 0.38 | 0.18 | 235.25 |
| 13 + 37 (1:1) | 0.67 | 1.25 | 2.86 | 167.82 |

[a]Inhibitory concentrations (IC$_{50}$) represent the average of triplicate determinations;
[b]Concentration of the compound required to cause microsopically visible change or disruption in about 50% of the cell sheet; and
[c]Not active up to 128 μg/mL.

It can be seen from Table 3 that compounds 12, 13, 40 and 42 of the present invention all exhibit antiviral activity against herpes simplex type 1 virus (HSV-1), herpes simplex type 2 virus (HSV-2) and varicella-zoster virus (VZV) in Hela cell culture with the exception that compound 40 is not active against VZV. Moreover, compounds 12, 13, 40 and 42 synthezied in the present invention have a lower cellular toxicity in comparison with that of Ara-A 37 compound.

Adenosine deaminase can form a complex with acyclonucleoside VI and arabinoside 37 (Table 1), thus their antiviral activity is decreased. Compound 13 of the present invention inhibits adenosine deaminase (Table 1). As a result of this inhibition, a synergistic effect on the antiviral activity of VI and Ara-A 37 by mixing with compound 13 was predicted and was observed (Table 3).

The ability of a drug to penetrate a membrane and to exhibit biological activity is correlated to its lipophilicity (Tables 2 and 3). The phosphonoamidate derivative 42 as a lipophilic pro-drug, which displayed superior antiviral activity (Table 3). The activity increment of 42 over acyclic nucleoside phosphonate 13, Ara-A 37, and dinucleotide phosphonate 40 may be due to a combination of increased lipophilicity and resistance to adenosine deaminase (Tables 1–3). We hypothesize that, as a masked membrane-soluble form of the bioactive nucleotide analog 40, phosphonoamidate 42 may act as a proteinase substrate. With the aid of phosphodiesterases, the biologically active compounds 13 and 37 were then liberated as potential drugs, and were effective against infected cells (Table 3).

The embodiments of the present invention described above are to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. An adenylate analog having the following formula:

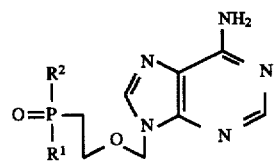

wherein $R^1$ is hydroxyl, $C_1$–$C_4$ alkoxy, an amino ester radical of —NH—$R^3$—COOR$^4$, wherein $R^3$ is a bivalent $C_1$–$C_4$ saturated hydrocarbon and $R^4$ is $C_1$–$C_4$ alkyl; and $R^2$ is hydroxyl, —O⁻NH$_4^+$ or

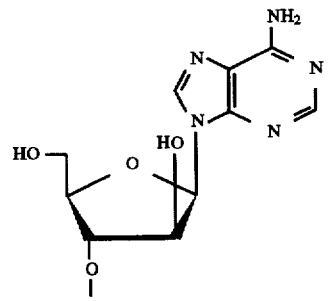

or a pharmaceutically acceptable salt thereof.

2. The adenylate analog as defined in claim 1, wherein $R^2$ is:

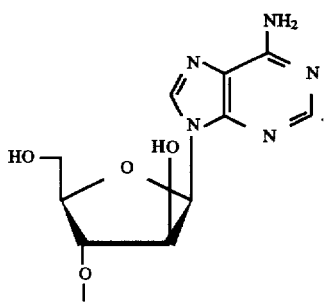

3. The adenylate analog as defined in claim 1, wherein $R^1$ is methyl L-alaninate ((L)-NHCHCH$_3$CO$_2$CH$_3$).

4. The adenylate analog as defined in claim 2, wherein $R^1$ is methyl L-alaninate ((L)-NHCHCH$_3$CO$_2$CH$_3$).

5. A pharmaceutical composition comprising a therapeutically effective amount of the adenylate analog as defined in claim 1 or a pharmaceutically acceptable salt therof, as an active ingredient, in admixture with a pharmaceutically acceptable carrier or diluent.

6. The pharmaceutical composition as defined in claim 5, wherein $R^2$ is:

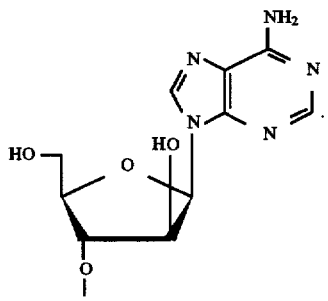

7. The pharmaceutical composition as defined in claim 5, wherein $R^1$ is methyl L-alaninate ((L)-NHCHCH$_3$CO$_2$CH$_3$).

8. The pharmaceutical composition as defined in claim 6, wherein $R^1$ is methyl L-alaninate ((L)-NHCHCH$_3$CO$_2$CH$_3$).

9. A method for the treatment of a human infected by a herpes simplex virus comprising administering a therapeutically effective amount of the adenylate analog as defined in claim 1 to a human infected by a herpes simplex virus.

10. The method as defined in claim 9, wherein $R^2$ is:

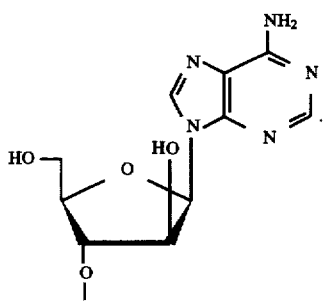

11. The method as defined in claim 10, wherein $R^1$ is methyl L-alaninate ((L)-NHCHCH$_3$CO$_2$CH$_3$).

12. The method as defined in claim 11, wherein $R^1$ is methyl L-alaninate ((L)-NHCHCH$_3$CO$_2$CH$_3$).

* * * * *